United States Patent
van de Haar

(10) Patent No.: US 6,751,283 B2
(45) Date of Patent: Jun. 15, 2004

(54) RECONSTRUCTION METHOD FOR TILTED-GANTRY COMPUTED TOMOGRAPHY

(75) Inventor: Peter G. van de Haar, Eindhoven (NL)

(73) Assignee: Koninklijke Philips Electronics, N.V., Eindhoven (NL)

(*) Notice: Subject to any disclaimer, the term of this patent is extended or adjusted under 35 U.S.C. 154(b) by 45 days.

(21) Appl. No.: 10/213,467

(22) Filed: Aug. 6, 2002

(65) Prior Publication Data
US 2004/0028173 A1 Feb. 12, 2004

(51) Int. Cl.⁷ ................................. A61B 6/03
(52) U.S. Cl. .................... 378/17; 378/15; 378/901
(58) Field of Search ................... 378/4, 15, 17, 378/901

(56) References Cited

U.S. PATENT DOCUMENTS

| | | | |
|---|---|---|---|
| 6,061,420 A | 5/2000 | Strong et al. | 378/4 |
| 6,240,157 B1 | 5/2001 | Danielsson | 378/15 |
| 6,275,561 B1 | 8/2001 | Danielsson | 378/15 |
| 6,285,733 B1 | 9/2001 | Proksa et al. | 378/15 |
| 6,324,246 B1 * | 11/2001 | Ruimi | 378/15 |

FOREIGN PATENT DOCUMENTS

| | | |
|---|---|---|
| EP | 0 981 995 | 3/2000 |
| EP | 981 996 A1 | 3/2000 |
| EP | 1 085 467 | 3/2001 |
| EP | 113 397 A2 | 7/2001 |
| WO | WO 02/30282 A2 | 4/2002 |
| WO | WO 02/43565 A1 | 6/2002 |

OTHER PUBLICATIONS

Hsieh, "Tomographic Reconstruction for Tilted Helical Multislice CT", IEEE Trans. on Med. Imaging, Vol. 19, No. 9, Sep. 2000, pp. 864–872.

Proksa, et al., "The n–PI Method for Helical Cone–Beam CT", IEEE Trans. on Med. Imaging, Vol. 19, No. 9, Sep. 2000, pp. 848–863.

* cited by examiner

*Primary Examiner*—David Bruce
(74) *Attorney, Agent, or Firm*—Fay, Sharpe, Fagan, Minnich & McKee, LLP

(57) ABSTRACT

A computed tomography apparatus (10) for performing volumetric helical imaging acquires helical computed tomography imaging data (72) using a tilted gantry geometry. In the tilted gantry geometry, a rotational plane of a rotating radiation source (16) is tilted at an angle ($\chi$) with respect to a direction (Z) of linear motion of a subject. A transform processor (40) transforms (74) the imaging data (72) to a zero tilt geometry. A rebinning processor (50) rebins (110) the transformed imaging data (76) to a non-sheared detector window. A reconstruction processor (54) reconstructs (130) the transformed and rebinned imaging data (112) to generate a three-dimensional image representation (132). Optionally, an image transform processor (56) transforms (134) the reconstructed image representation (132) with an inverse of the zero tilt geometry transformation (74).

26 Claims, 7 Drawing Sheets

RECONSTRUCTION METHOD FOR TILTED-GANTRY COMPUTED TOMOGRAPHY

BACKGROUND OF THE INVENTION

The present invention relates to the diagnostic imaging arts. It particularly relates to helical volumetric computed tomography (CT) imaging employing a geometric configuration in which the gantry is tilted relative to its axis of rotation, and will be described with particular reference thereto. However, the invention will also find application in other types of tomographic volumetric imaging using tilted geometric configurations.

Computed tomography (CT) imaging employs a radiation source, typically an x-ray source, that generates a fan-beam or cone-beam of x-rays that traverse an examination region. A subject arranged in the examination region interacts with and absorbs a portion of the traversing x-rays. In volume imaging, a two-dimensional detector array is arranged opposite the x-ray source to detect and measure intensities of the transmitted x-rays. Typically, the x-ray source and the detector array are mounted at opposite sides of a rotating gantry and rotate together as the gantry is rotated to acquire data over an angular range of projection views.

In helical CT imaging, the subject is advanced linearly through the examination region along a direction that is perpendicular to the gantry rotation plane such that the x-ray source traverses a helical trajectory relative to the subject. X-ray absorption data acquired during the helical orbiting is reconstructed using any of several known three-dimensional reconstruction methods such as an approximate n-PI filtered backprojection reconstruction method, an exact n-PI reconstruction method, or the like. The selected reconstruction generates a three-dimensional image representation of the subject or of a selected portion thereof.

In certain medical diagnostic applications of helical CT imaging, it is desirable to use a tilted gantry geometry in which the gantry rotation plane is tilted respective to the linear patient advancement direction. For example, in imaging of the head a substantial gantry tilt of up to 30° beneficially reduces radiation exposure of radiation-sensitive eye tissues. For imaging curvilinear anatomical structures such as the spine the gantry is beneficially dynamically tilted during imaging to keep the scanned structure generally perpendicular to the rotating gantry.

A problem arises because the tilted geometry results in a sheared helical trajectory of the x-ray source. The shearing is not accounted for in conventional helical computed tomography reconstruction techniques, and leads to substantial image degradation.

The present invention contemplates an improved apparatus and method that overcomes the aforementioned limitations and others.

SUMMARY OF THE INVENTION

According to one aspect of the invention, an apparatus is disclosed for generating an image representation of an imaged subject from volumetric helical computed tomography imaging data acquired using a tilted gantry geometry. A means is provided for transforming the imaging data to a zero tilt geometry. A means is provided for rebinning the transformed imaging data to a non-sheared detector window. A means is provided for reconstructing the transformed and rebinned imaging data to generate a three-dimensional image representation.

According to another aspect of the invention, a method is provided for generating an image representation of an imaged subject from volumetric helical computed tomography imaging data acquired using a tilted gantry geometry. The imaging data is transformed to a zero tilt geometry. The transformed imaging data is rebinned to a non-sheared detector window. The transformed and rebinned imaging data is reconstructed to generate a three-dimensional image representation.

According to yet another aspect of the invention, an apparatus is disclosed for performing volumetric helical computed tomography imaging of a subject. A computed tomography scanner acquires helical computed tomography imaging data using a tilted gantry geometry. In the tilted gantry geometry, a rotational plane of a rotating radiation source is tilted with respect to a direction of linear motion of the subject. A transform processor transforms the imaging data to a zero tilt geometry. A rebinning processor rebins the transformed imaging data to a non-sheared detector window. A reconstruction processor reconstructs the transformed and rebinned imaging data to generate a three-dimensional image representation.

One advantage of the present invention resides in simplified reconstruction of computed tomography imaging data acquired using a tilted gantry configuration.

Another advantage of the present invention resides in transforming tilted gantry computed tomography imaging data to a zero tilt geometry which is readily reconstructed by any of a variety of reconstruction techniques.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

DETAILED DESCRIPTION OF THE PREFERRED EMBODIMENTS

Figure 1:
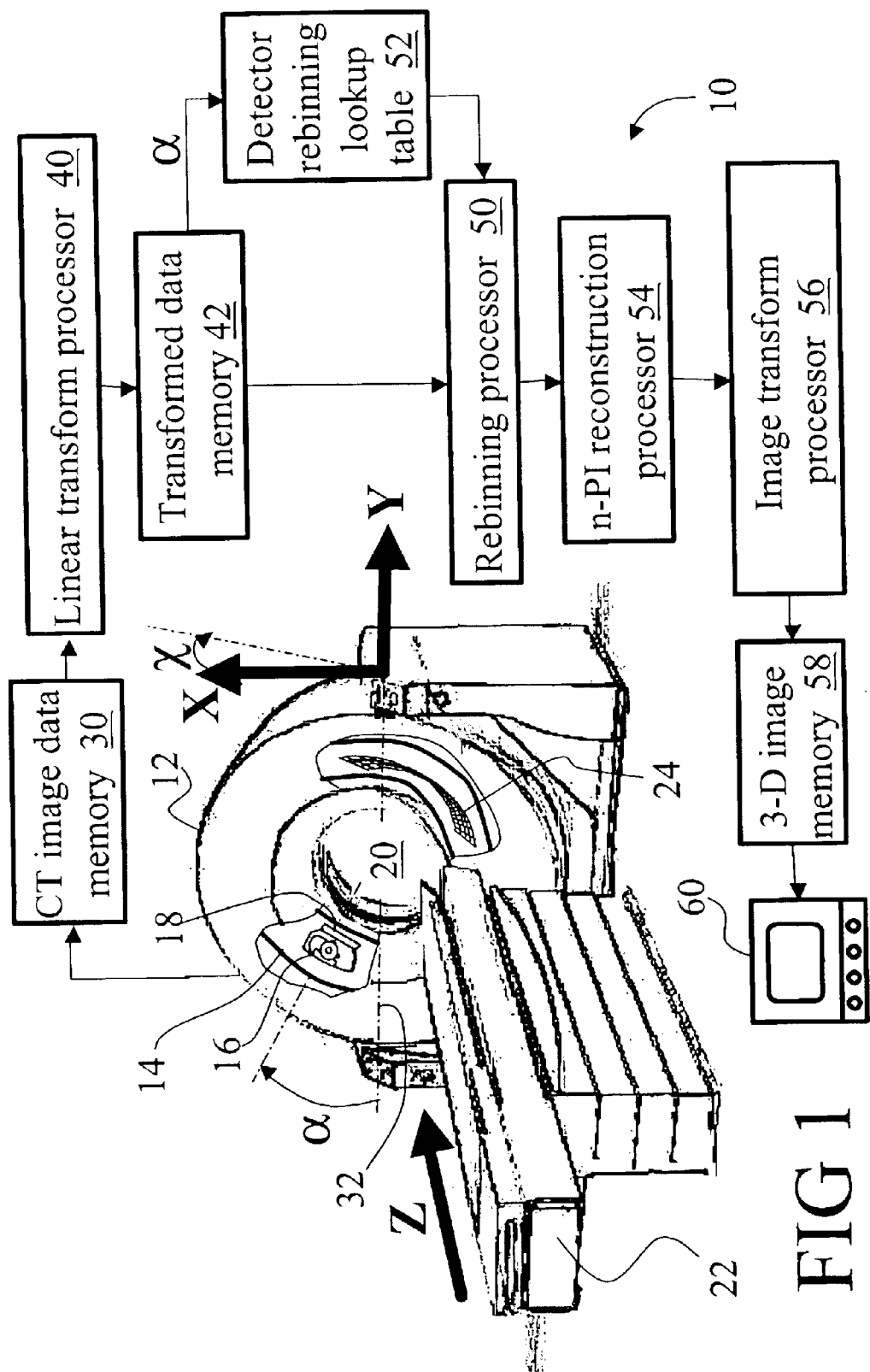
FIG. 1 schematically shows an exemplary computed tomography (CT) imaging apparatus according to one embodiment of the invention. Portions of the CT gantry are shown partially cut-out to reveal selected radiation source and detector components mounted on the gantry.

With reference to FIG. 1, a computed tomography (CT) imaging apparatus or scanner 10 includes a tiltable stationary gantry 12 which houses a rotating gantry 14 that supports an x-ray source 16 and a collimator 18 (shown in partial cut-away). The x-ray source 16 and collimator 18 cooperate to produce a fan-shaped, cone-shaped, wedge-shaped, or otherwise-shaped x-ray beam directed across an examination region 20. It is to be appreciated that other types of radiation sources besides an x-ray source can also be used. An angular orientation of the x-ray source 16 around the stationary gantry 12 is designated by an angular coordinate or position α. A patient or other subject is arranged on a subject support 22 which is linearly movable in a Z-direction.

A two-dimensional detector array 24 (shown in partial cut-away) is arranged across the examination region 20 opposite the x-ray source 16 to receive x-rays produced by the source 16 after traversing the examination region 20. The x-ray source 16 and the detector array 24 are arranged in fixed relative position and rotate together with the rotating gantry 14.

The detector array 24 detects transmitted x-ray intensities by converting the received x-rays into electrical signals, optical signals, or the like. In one suitable detector arrangement, a scintillator converts x-rays to scintillation events whose position and intensity are measured by an array of photodiodes, photodetectors, or the like. The detector signals are ported off the rotating gantry 14 using a slip ring arrangement, a radio frequency electromagnetic transmitter, or the like (not shown). In one suitable arrangement, electrical photodetector signals are converted to optical signals which are transmitted off the gantry via one or more fiber optical couplings of a slip ring. An electrical slip ring coupling can also be used. The x-ray data along with gantry angle, patient support, and detector array coordinates are formatted and stored in a CT image data memory 30.

With continuing reference to FIG. 1, the stationary gantry 12, and hence the rotating gantry 14, is tiltable about a tilt axis 32, corresponding to a Y-direction in FIG. 2 which is orthogonal to the Z-direction. The gantry tilt is designated by a tilt angle χ referenced to an X-direction which is orthogonal to the Y- and Z-directions. In a preferred helical CT imaging configuration, the x-ray source 16 and the detector array 24 rotate together in fixed relative position at a selected rotation rate. Alternatively, the x-ray source 16 rotates with the rotating gantry 14 and a band of detector arrays is mounted in stationary fashion to the stationary gantry circumscribing the rotating gantry. The subject support 22 simultaneously advances the patient or other subject linearly in the Z-direction as the x-ray source 16 rotates to define the helical trajectory.

Figures 2A, 2B:
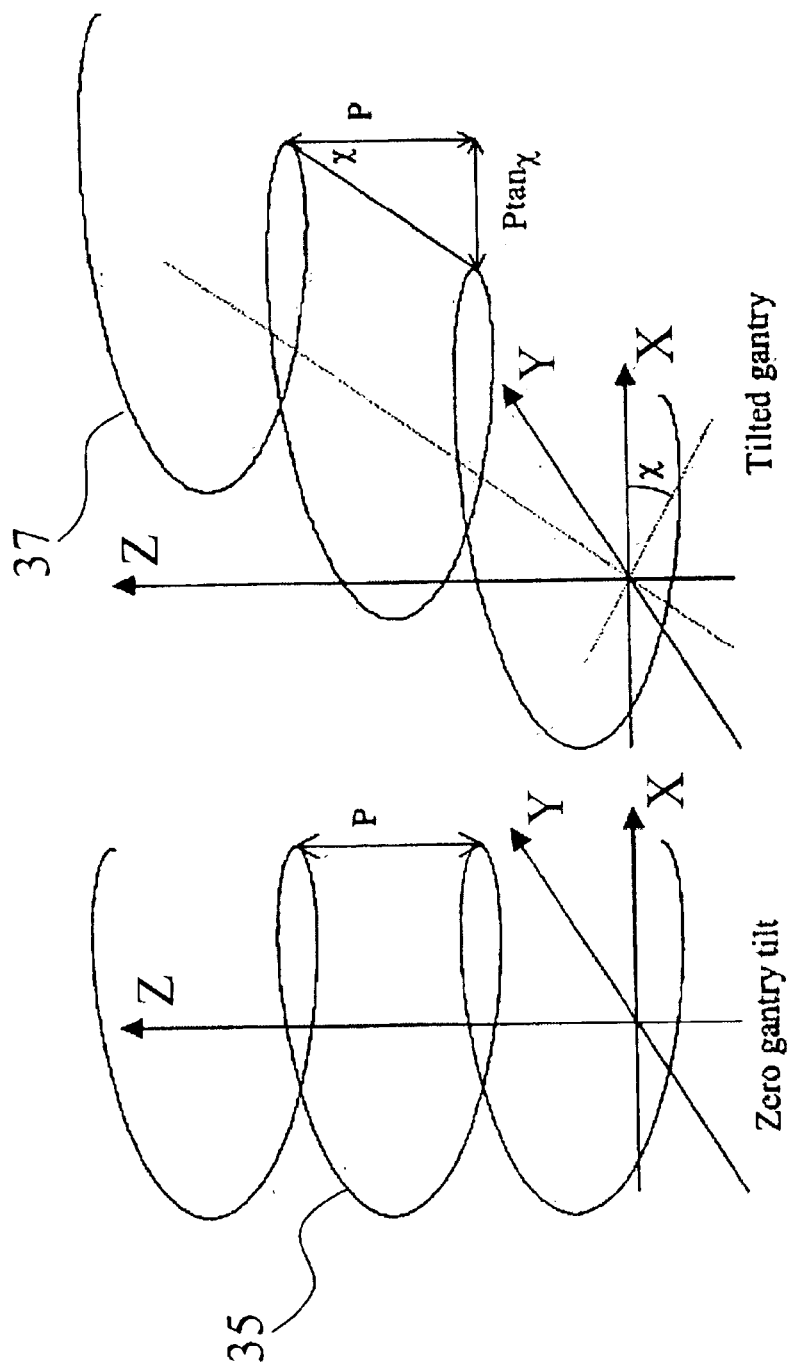
FIG. 2A shows a perspective view of a pure helical radiation source path in a zero tilt helical volumetric computed tomography geometry imaging scan.
FIG. 2B shows a perspective view of a sheared helical radiation source path in a tilted gantry helical volumetric computed tomography geometry imaging scan.
Figure 3:
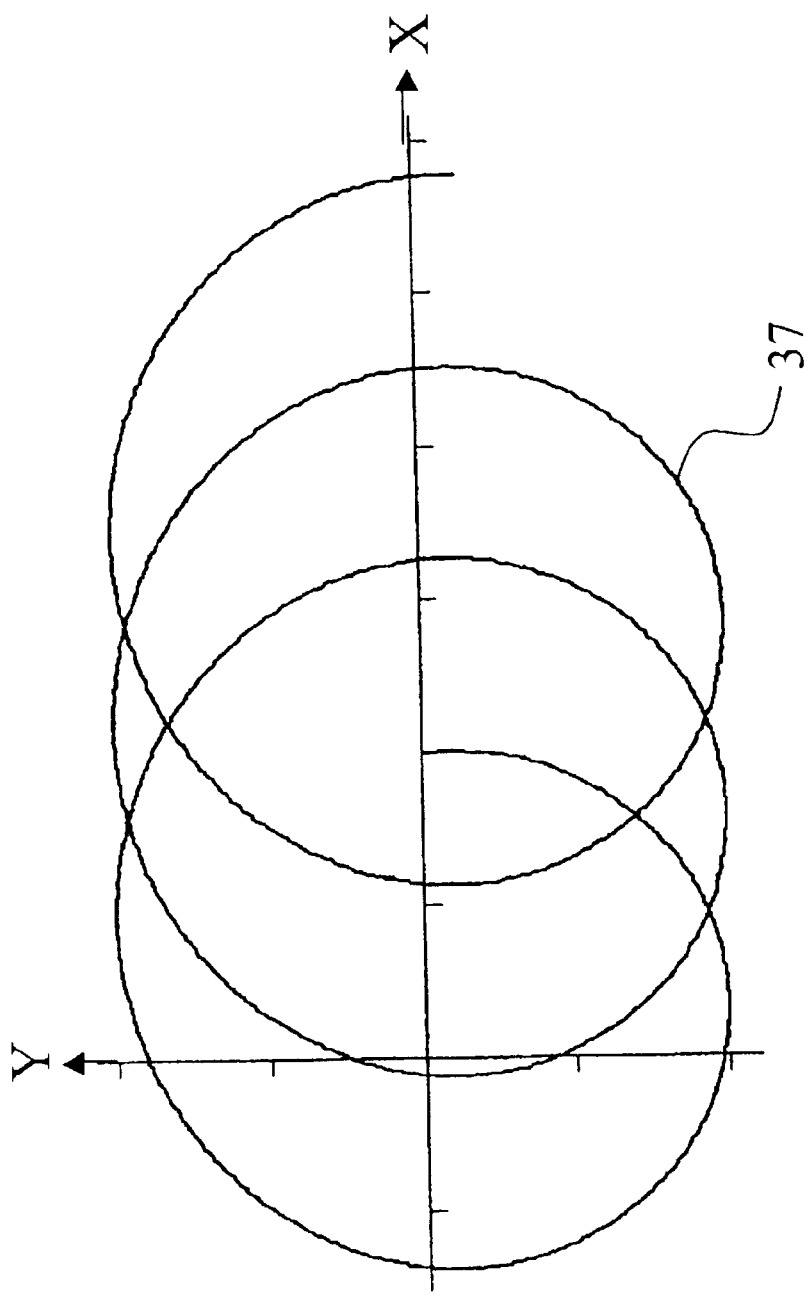
FIG. 3 shows a view looking along the Z-direction of the sheared helical radiation source path of FIG. 2B.

With continuing reference to FIG. 1 and with further reference to FIGS. 2A, 2B, and 3, a zero gantry tilt configuration χ=0°, with uniform rotation and linear advancement rates (i.e., constant dα/dt and dZ/dt rates) results in a pure or right helical trajectory 35 of the x-ray source 16 relative to the subject, with the helical axis parallel to the Z-direction. For a non-zero gantry tilt, χ≠0°, and uniform gantry rotation and subject advancement rates, a sheared helical trajectory 37 of the x-ray source 16 results, in which the helix is sheared in the X-direction by the tilt angle χ. For this reason, the tilt angle χ is also referred to herein as shear angle χ. In presently existing tilted gantry CT imaging scanners, the gantry can typically be tilted over an angular range of about χ=−30° to χ=+30°. However, larger tilt angles χ are also contemplated.

With continuing reference to FIGS. 1, 2A, 2B, and 3, the pure and sheared helical trajectories 35, 37 have a pitch P determined by an interrelation between the rotation rate of the x-ray source 16 and the rate of linear advancement of the subject support 22. The pitch P is given by:

$$P = 2\pi p \qquad (1),$$

where p is a constant and the pitch P is the linear distance the source moves along the Z-direction for 360° of rotation.

For the purpose of describing the helical CT geometry, coordinates of the form $(x\ y\ z)^T$ are used, in which x corresponds to a coordinate in the X-direction, y corresponds to a coordinate in the Y-direction, z corresponds to a coordinate in the Z-direction, and T is the matrix transpose operator. In the case of a pure helical trajectory 35 of the radiation source 16, a position of the x-ray source 16 in the coordinate system of the X-, Y-, and Z-directions is given by:

$$\vec{S}(\alpha) = \begin{pmatrix} S\cos\alpha \\ S\sin\alpha \\ p\alpha \end{pmatrix}, \qquad (2)$$

where α is the previously defined angular position of the x-ray source 16, S is a distance between the source 16 and a center of rotation which generally corresponds with a center of the examination region 20, and p is the helical constant previously defined with reference to equation (1).

In the case of a sheared helical trajectory 37, a position of the x-ray source 16 in the coordinate system of the X-, Y-, and Z-directions is given by:

$$\vec{S}(\alpha) = \begin{pmatrix} S\cos\alpha + p\alpha\tan\chi \\ S\sin\alpha \\ p\alpha \end{pmatrix}, \qquad (3)$$

where it will be noticed that only the coordinate in the X-direction is modified by the gantry tilt X. Hence, the x coordinate is referred to herein as a sheared coordinate.

With continuing reference to FIG. 1, the tilted geometry imaging data is processed by a linear transform processor 40 that transforms the imaging data into a zero tilt geometry as described in greater detail below. The transformed imaging data is stored in a transformed data memory 42. The transformed data is processed by a rebinning processor 50 to rebin the transformed data to a focus-centered (FC) detector window defined in the zero tilt geometry. In a preferred embodiment, the rebinning processor 50 accesses a detector rebinning lookup table 52 to obtain source angle α-dependent detector coordinates for the rebinning.

The transformed and detector-rebinned imaging data is suitably processed by a reconstruction processor 54, which preferably implements an n-PI reconstruction, such as an exact n-PI reconstruction or an approximate n-PI filtered backprojection reconstruction, to produce an image representation.

As is known in the art, an n-PI reconstruction is suitable for reconstructing helical computed tomography imaging data acquired using pure helical orbiting 35 of the radiation source 16. As used herein, n-PI reconstruction methods include methods with n=1 which are also commonly called PI reconstruction methods. In the apparatus 10, the n-PI reconstruction is suitably applied by the reconstruction processor 54 to tilted gantry imaging data which has been transformed to a zero tilt geometry by the linear transform processor 40 and rebinned to a focus-centered detector in the zero tilt geometry by the rebinning processor 50.

Although an n-PI reconstruction method is preferred, other volumetric helical computed tomography reconstruction methods that suitably reconstruct purely helical CT imaging data can instead be performed by the reconstruction processor 54.

With continuing reference to FIG. 1, it will be recognized that the image representation produced by the reconstruction processor 54 will be sheared by an angle $-\chi$ in the X-direction due to the action of the linear transform processor 40. Hence, an image transform processor 56 preferably transforms the image representation in the zero tilt geometry back to the tilted gantry geometry. The image representation in the tilted gantry geometry is stored in a three-dimensional image memory 58, and is optionally processed to construct a three-dimensional rendering, to extract selected slices, to compute a maximum intensity projection, or the like, which is displayed on a video, active matrix, CCD, monitor 60 or other display device.

Figure 4:
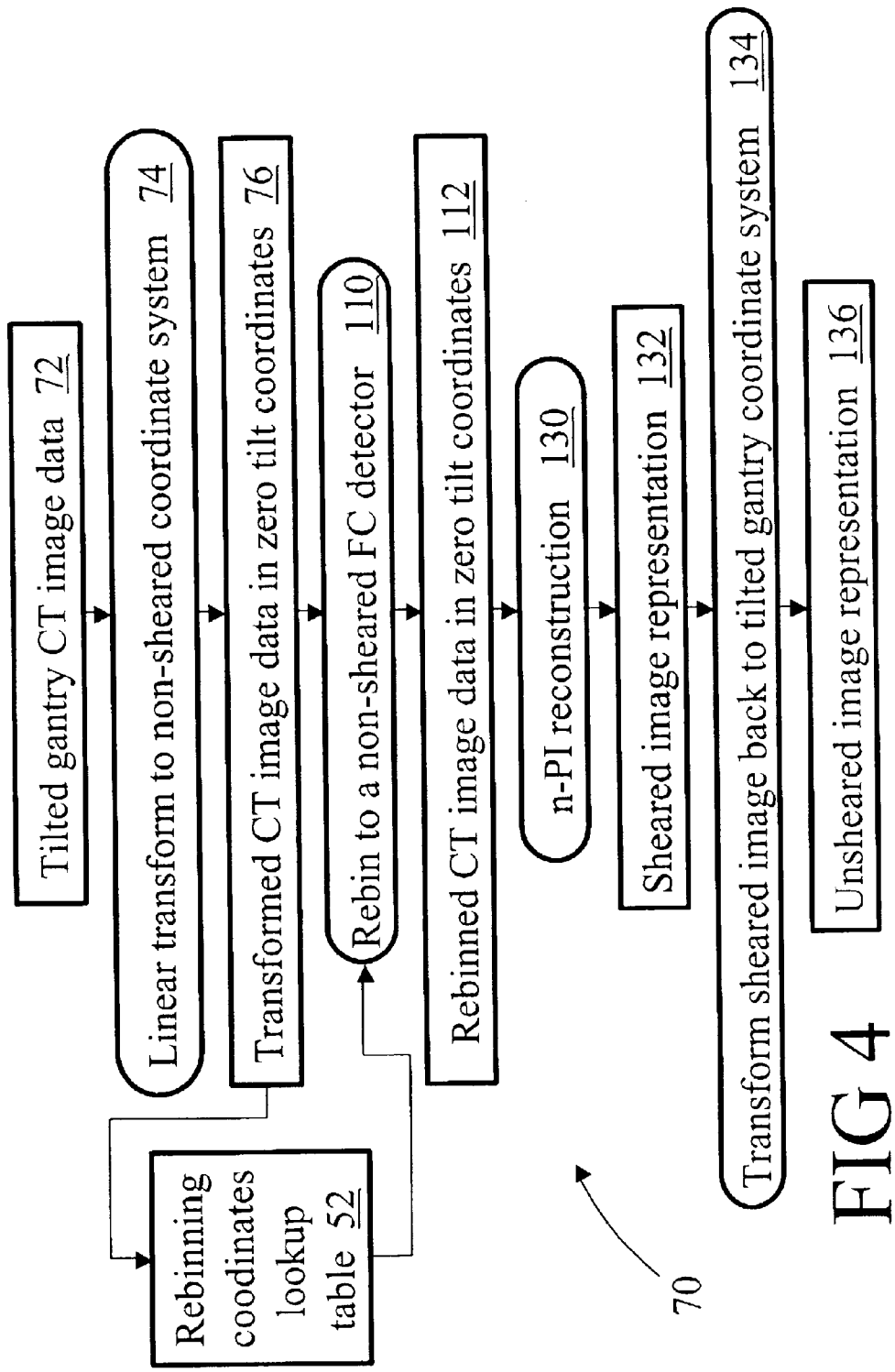
FIG. 4 shows a preferred method for reconstructing tilted gantry computed tomography data.

With continuing reference to FIG. 1 and with further reference to FIG. 4, an image reconstruction method 70 suitably implemented by the combination of the linear transform processor 40, rebinning processor 50, reconstruction processor 54, and image transform processor 56 is described. Tilted gantry CT imaging data 72 stored in the CT image data memory 30 is processed by the linear transform processor 40 to linearly transform the imaging data 72 to a non-sheared coordinate system in a step 74 to produce non-sheared imaging data 76 in a zero tilt geometry which is stored in the transformed data memory 42. Comparison of equations (2) and (3) above shows that the tilted gantry coordinates $(x'\ y'\ z')^T$ are related to a zero tilt coordinate system $(x\ y\ z)^T$ by a linear transform:

$$\begin{pmatrix} x' \\ y' \\ z' \end{pmatrix} = \begin{pmatrix} x + p\alpha\tan\chi \\ y \\ z \end{pmatrix} = \begin{pmatrix} x + z\tan\chi \\ y \\ z \end{pmatrix} \quad (4)$$

It will be noted that only the coordinate in the X-direction is linearly transformed by the coordinates transformation of equation (4). The coordinates y and z in the Y- and Z-directions, respectively, are unchanged. Hence, the sheared coordinate in the X-direction of the tilted gantry image data 72 is linearly transformed according to:

$$x_{zt}=x_{sh}-p\alpha\tan(\chi)=x_{sh}-z\tan(\chi) \quad (5)$$

where $x_{sh}$ is the sheared coordinate in the X-direction in the image data 72, z the coordinate in the Z-direction (z has the same value in both the sheared and the zero tilt coordinate systems), $\chi$ is the shear angle, and $x_{zt}$ is the coordinate in the X-direction transformed into the zero tilt geometry.

Figure 5:
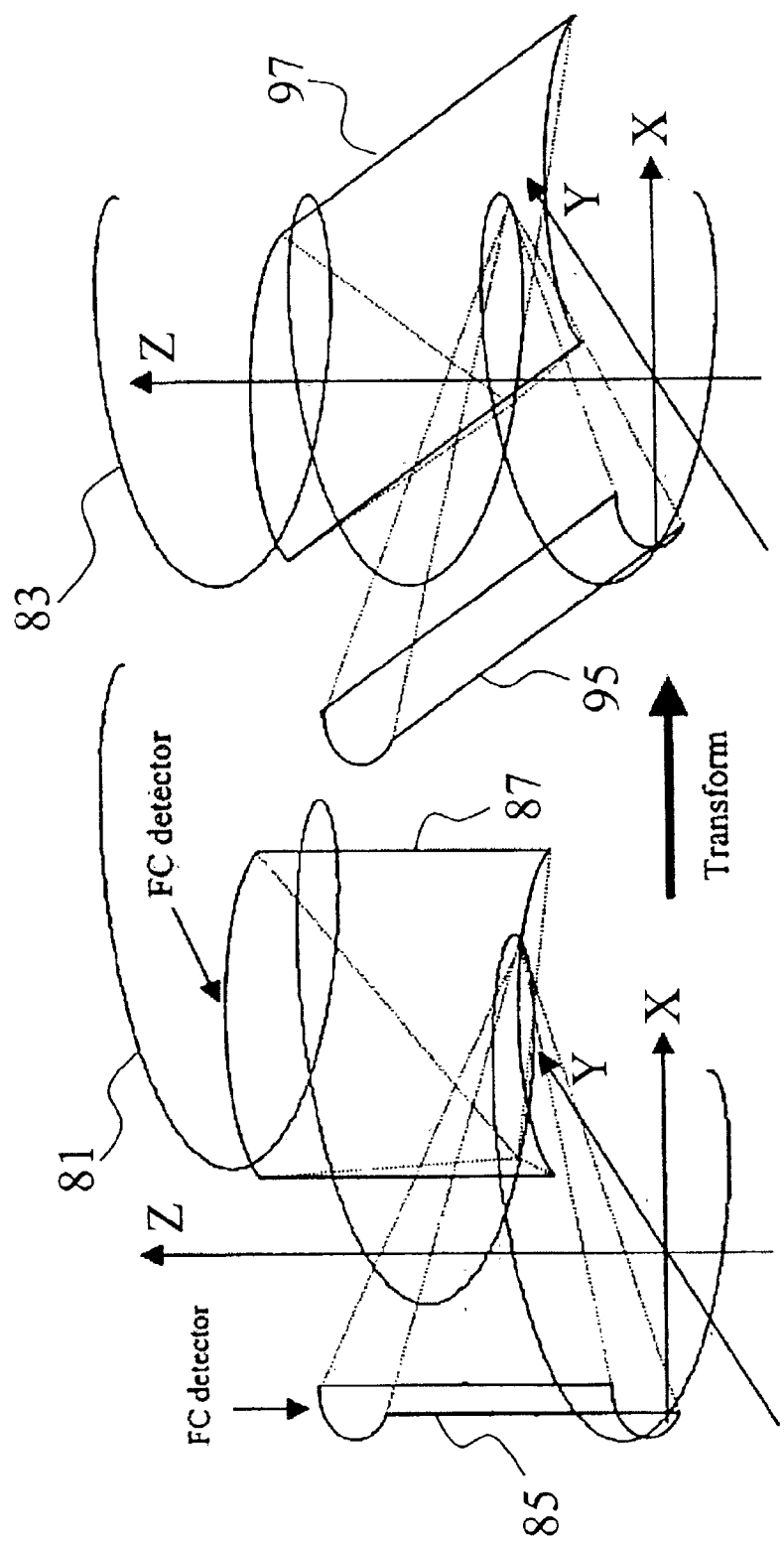
FIG. 5 schematically illustrates a linear transform of tilted gantry computed tomography imaging data to a zero tilt geometry.

The transformation of equations (4) and (5) is diagrammatically illustrated in FIG. 5. A source path 81 followed by the x-ray source 16 is transformed by equations (4) and (5) into a purely helical path 83 in the zero tilt geometry. Furthermore, because the coordinate system transform of equations (4) and (5) is purely linear, it follows that the PI lines, PI surfaces, and PI and n-PI detectors used in deriving PI and n-PI reconstructions also exist in the transformed zero tilt geometry. In other words, a transformed ray remains a ray.

With continuing reference to FIGS. 1, 4, and 5, the transformations of equations (4) and (5) distort the detector window. Two positions 85, 87 of a physical focus-centered detector are shown in FIG. 5, corresponding to two positions of the x-ray source 16. For simplicity in physical construction and typically reduced complexity of image reconstruction, physical radiation detectors in computed tomography typically include straight sides, i.e. are rectangular. However, the corresponding detector positions 95, 97 in the zero tilt geometry are sheared.

Figure 6:
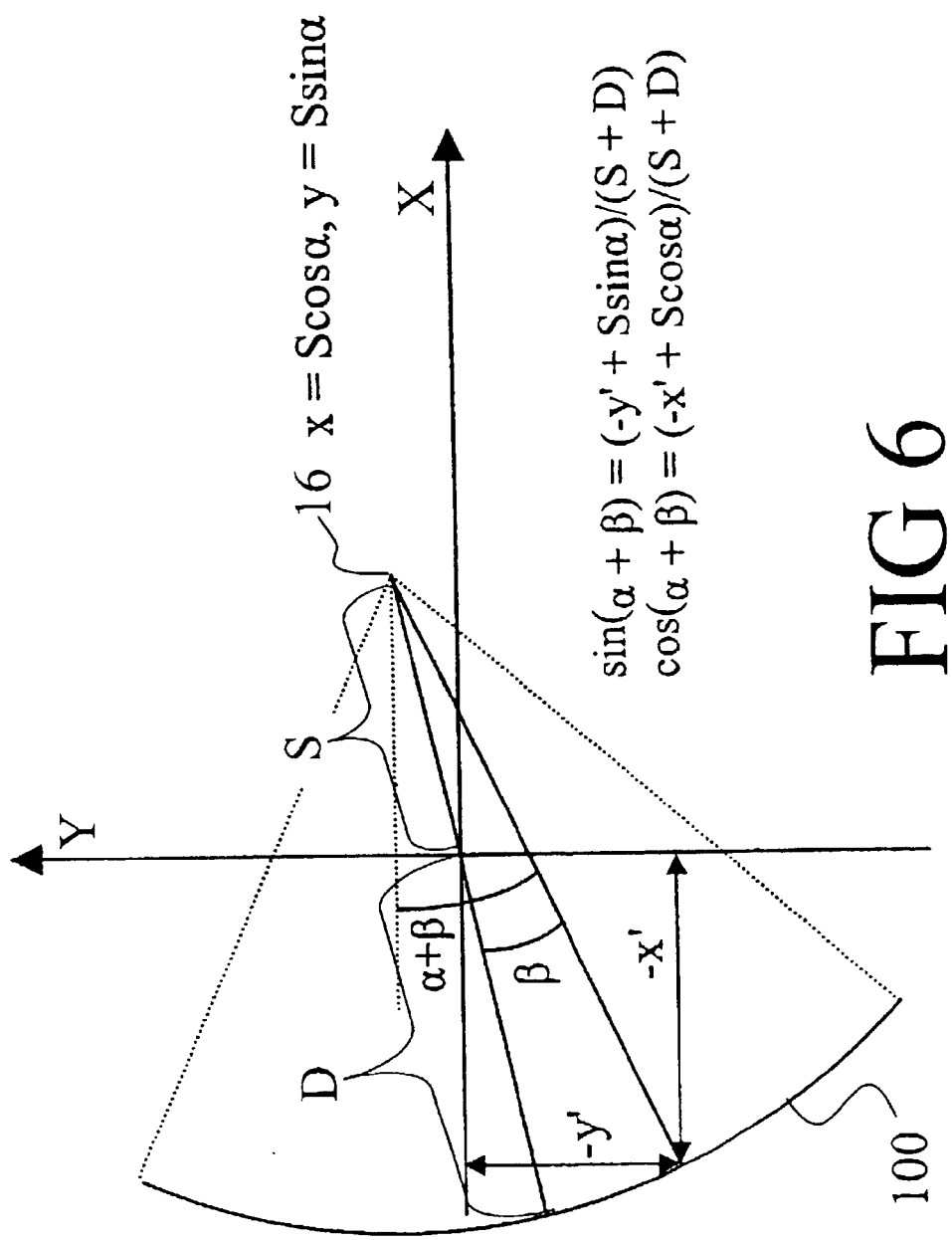
FIG. 6 diagrammatically shows a determination of the position of a focus-centered detector surface in a non-tilted geometry.

With continuing reference to FIG. 5 and with is further reference to FIG. 6 which shows a projection 100 of a focus-centered detector in a pure helix orbit ($\chi=0$) onto a plane defined by the X- and Y-directions, the rectangular focus-centered detector surface is given by;

$$\vec{x}_{FC}(\alpha, \beta, g, \chi = 0) = \begin{pmatrix} S\cos\alpha - (S + D)\cos(\alpha + \beta) \\ S\sin\alpha - (S + D)\sin(\alpha + \beta) \\ g + p\alpha \end{pmatrix}, \quad (6)$$

where: D is a distance between the center of rotation (the intersection of the X- and Y-directions in FIG. 6, generally corresponding with a center of the examination region 20) and a center of the focus-centered detector 100; S is the distance between the x-ray source 16 and the center of rotation as defined previously; $\alpha$ is the rotational coordinate of the x-ray source 16 as defined previously, $\beta$ is an angular position of a ray which impinged upon the detector 100 at coordinates (-x, -y); and g is a detector coordinate in the Z-direction.

The fan angle of the x-ray beam is $2\beta_{max}$ where $\beta_{max}$ and $-\beta_{max}$ are the angular positions of the outermost rays in the x-ray beam fan. The focus-centered detector is bounded by the fan angle range $[-\beta_{max}, \beta_{max}]$ and by boundaries $[-g_{max}, g_{max}]$ in the Z-direction.

In the case of a tilted gantry, the detector surface of equation (6) is modified by the position of the x-ray source 16 which is given by equation (3) for a tilted gantry. The rectangular focus-centered detector surfaces 85, 87 are given by:

$$\vec{x}_{FC}(\alpha, \beta, g, \chi) = \begin{pmatrix} S\cos\alpha - (S + D)\cos(\alpha + \beta) + p\alpha\tan\chi \\ S\sin\alpha - (S + D)\sin(\alpha + \beta) \\ g + p\alpha \end{pmatrix}, \quad (7)$$

where the limits on the parameters $\beta$ and g are given by the fan angle range $[-\beta_{max}, \beta_{max}]$ and by $[-g_{max}, g_{max}]$, respectively. The transformation:

$$\begin{pmatrix} x' \\ y' \\ z' \end{pmatrix} = \begin{pmatrix} x - p\alpha\tan\chi \\ y \\ z \end{pmatrix} = \begin{pmatrix} x - z\tan\chi \\ y \\ z \end{pmatrix} \quad (8)$$

transforms a sheared helix back to a non-sheared helix. For the sheared focus-centered detector the coordinate $z=g+p\alpha$ and so the transformation becomes:

$$\begin{pmatrix} x' \\ y' \\ z' \end{pmatrix} = \begin{pmatrix} x - (g + p\alpha)\tan\chi \\ y \\ z \end{pmatrix}, \quad (9)$$

so that the transformed focus-centered detector surfaces 95, 97 have the shape:

$$\vec{x}_{FC}(\alpha, \beta, g, \chi) = \begin{pmatrix} S\cos\alpha - (S + D)\cos(\alpha + \beta) - g\tan\chi \\ S\sin\alpha - (S + D)\sin(\alpha + \beta) \\ g + p\alpha \end{pmatrix}, \quad (10)$$

where again the limits on the parameters $\beta$ and g are given by the fan angle range $[-\beta_{max}, \beta_{max}]$ and by $[-g_{max}, g_{max}]$, respectively. It is seen in equation (10) that the columns of the focus-centered detector surfaces 95, 97 have become sheared, as also seen in FIG. 5. That is, a column given by a selected ($\alpha$, $\beta$) has a g-dependent coordinate in the X-direction. The columns are sheared at the tilt angle $\chi$.

Figure 7:
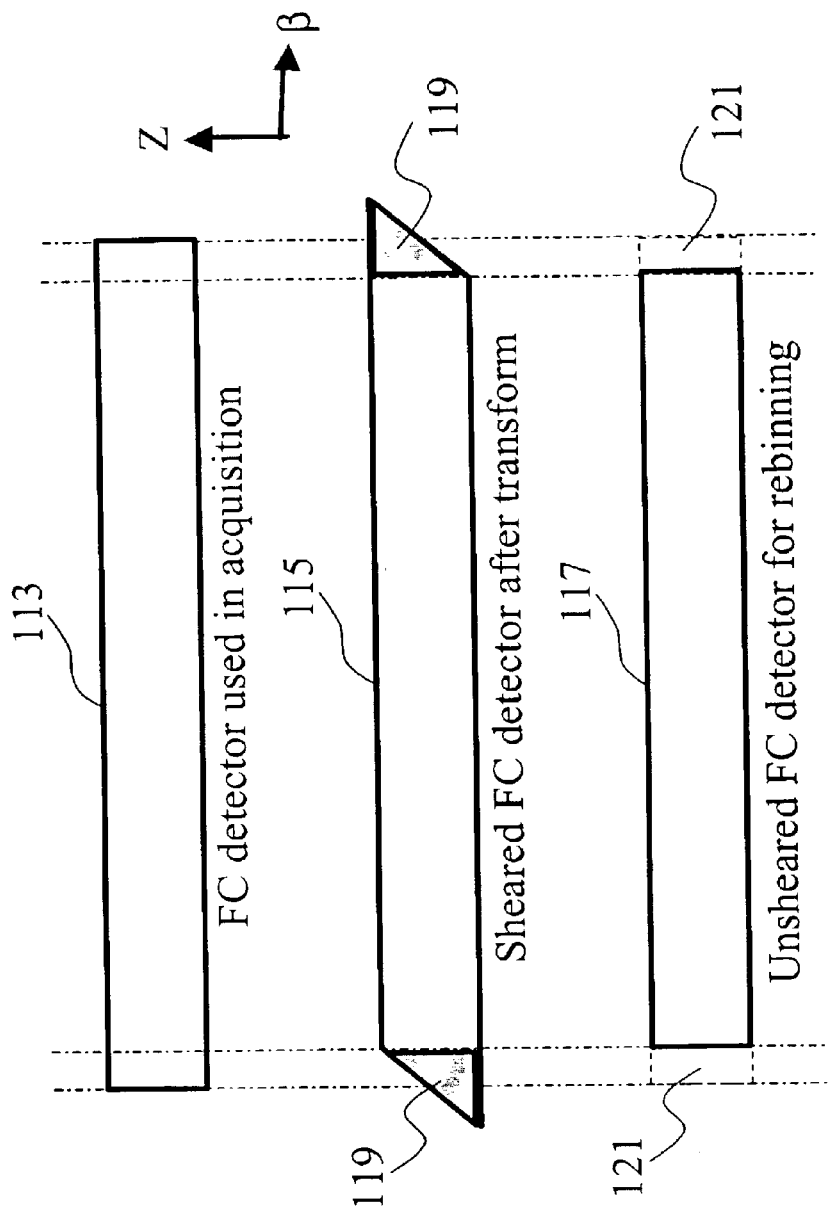
FIG. 7 diagrammatically illustrates an evolution of a focus-centered detector window during data acquisition, linear transformation, and rebinning.

With continuing reference to FIGS. 1 and 4 and with further reference to FIG. 7, the projection data 76 which has been transformed into the zero tilt coordinates is rebinned to a non-sheared focus-centered detector in a step 110 by the rebinning processor 50 to produce rebinned image data 112 in the zero tilt coordinate system. Computation of a suitable non-sheared focus-centered detector in the zero tilt coordinate system is described with reference to FIG. 7. Boundaries 113 of the physical focus-centered detector are transformed according to equation (9) to the sheared detector coordinate boundaries 115 in accordance with equation (10). A suitable window for rebinning has boundaries 117 shown in FIG. 7 which are obtained by removing the non-rectangular shear extensions 119, indicated by a cross-hatching in FIG. 7.

Comparison of the rebinning window boundaries 117 with the physical detector window boundaries 113 shows that the rebinning window has a reduced available fan angle, reduced by an amount 121 indicated in FIG. 7. However, for a typical focus-centered detector with a small height/width ratio (e.g., a detector with 20 rows along the Z-direction and 960 columns along the $\beta$ direction has a height/width ratio of about 0.04) the non-rectangular shear extensions 119 and the corresponding reduction 121 in fan angle will be small. The fan beam produced by the cooperating x-ray source 16 and collimator 18 is preferably reduced to conform with the reduced available fan angle of the rebinning window 117 to reduce radiation exposure of the subject.

With returning reference to FIG. 5, the transformed, sheared focus-centered detector windows 95, 97 are seen to have different amounts of shearing. In general, the shearing of a detector window will depend upon the rotational position $\alpha$ of the x-ray source 16.

Rebinning parameters are preferably stored in the rebinning coordinates lookup table 52. For a number $N_\alpha$ of projection views per helical rotation, $N_\alpha$ sets of rebinning coefficients are generally used. This number of rebinning coefficients is substantially larger than the number of coefficients used in common types of rebinning such as fan-to-parallel, equidistant, or height rebinning. Hence, in a preferred embodiment, the rebinning transform coefficients are functionally parameterized with respect to $\alpha$ so that the number of parameters stored in the rebinning coordinates lookup table 52 is substantially reduced. Because the detector shearing varies in a continuous fashion with the x-ray source angle coordinate $\alpha$, a suitable functional parameterization using a fitted continuous function is typically readily computable.

With reference to FIGS. 1 and 4, the transformed and rebinned imaging data 112 is processed by the reconstruction processor 54 in a step 130 to produce a sheared image reconstruction 132. A reconstruction method designed for purely helical computed tomography data is suitably employed. In the preferred embodiment, an n-PI reconstruction method is employed, where n is an odd integer such as n=1, n=3, or the like.

As is known in the art, a PI reconstruction employs a Tam-Danielsson detector window, also called a PI detector window, which extends between two neighboring turns of a helical source orbit. In the n-PI reconstruction framework, the Tam-Danielsson window is also called an n-PI window with n=1. In the n-PI reconstruction, the Tam-Danielsson window encompasses an odd number of turns, e.g. a 1-PI window (same as a PI window) extends from a first turn and terminates at a neighboring turn, while a 3-PI window extends from a first turn through neighboring and second-neighboring turns and terminates at a third-neighboring turn.

Those skilled in the art recognize that the n-PI window has beneficial characteristics for helical computed tomography image reconstruction. As the n-PI detector sweeps along a helical orbit, each point within a region of interest is sampled over 180° without redundant samplings. The 180° sampling is sufficient to perform an exact reconstruction, and the elimination of redundant samplings in the n-PI reconstruction improves reconstruction speed and computational efficiency for both exact and approximate reconstruction methods.

Various n-PI reconstruction methods are known which take advantage of the n-PI detector window, including both exact n-PI reconstructions and approximate n-PI filtered backprojection reconstruction methods. Because the transformed and rebinned imaging data 112 were obtained through processing by purely linear transformations, the PI lines, PI surfaces, and n-PI detector windows operating in the zero tilt geometry on the rebinned data 112 retain their beneficial properties.

The reconstruction step 130 produces the sheared image representation 132. Because the data was acquired with a tilted gantry geometry and transformed in the step 74 to the zero tilt geometry, it follows that the reconstructed image representation 132 exhibits a shear with a magnitude of the tilt or shear angle $\chi$. Hence, the image transform processor 56 in a step 134 transforms the sheared image representation 132 back to the original tilted gantry coordinate system to produce an unsheared image representation 136.

The transforming step 134 suitably employs a linear transform which is the inverse of the linear transform of equations (4) and (5). Only the coordinate in the sheared X-direction is transformed, according to:

$$x_{sh}=x_{zt}+p\alpha \tan(\chi)=x_{zt}+z \tan(\chi) \quad (11)$$

which is the inverse of the transform of equation (5). The unsheared image representation 136 is preferably stored in the three-dimensional image memory 58 for further processing such as graphical display rendering. However, for small shear angles $\chi$ and diagnostic tasks for which a small image shear is acceptable, it is also contemplated to omit the inverse transforming step 134 and store the sheared image representation 132 in the image memory 58.

The invention has been described with reference to the preferred embodiments. Obviously, modifications and alterations will occur to others upon reading and understanding the preceding detailed description. It is intended that the invention be construed as including all such modifications and alterations insofar as they come within he scope of the appended claims or the equivalents thereof.

Having thus described the preferred embodiments, the invention is now claimed to be:

1. An apparatus for generating an image representation of an imaged subject from volumetric helical computed tomography imaging data acquired using a tilted gantry geometry, the apparatus comprising:

a means for transforming the imaging data to a zero tilt geometry;

a means for rebinning the transformed imaging data to a non-sheared detector window; and a means for reconstructing the transformed and rebinned imaging data to generate a three-dimensional image representation.

2. A method for generating an image representation of an imaged subject from volumetric helical computed tomography imaging data acquired using a tilted gantry geometry, the method comprising:

transforming the imaging data to a zero tilt geometry;

rebinning the transformed imaging data to a non-sheared detector window; and reconstructing the transformed and rebinned imaging data to generate a three-dimensional image representation.

3. The method as-set forth in claim 2, wherein the transforming step includes:

linearly transforming a sheared coordinate.

4. The method as set forth in claim 3, wherein the sheared coordinate is perpendicular to a linear motion of the imaged subject.

5. The method as set forth in claim 3, wherein the linear transform of the sheared coordinate includes:

$$x_{zt} = x_{sh} - z \tan(\chi)$$

where $x_{sh}$ is the sheared coordinate, z is coordinate of a linear motion of the imaged subject, $\chi$ is a shear angle, and $x_{zt}$ is the sheared coordinate transformed to a zero tilt geometry.

6. The method as set forth in claim 3, further including:

linearly transforming the sheared coordinate of the three-dimensional image representation to recover the tilted gantry geometry.

7. The method as set forth in claim 2, wherein the transforming step includes applying a three-dimensional transform:

$$\begin{pmatrix} x' \\ y' \\ z' \end{pmatrix} = \begin{pmatrix} x + z\tan\chi \\ y \\ z \end{pmatrix}$$

where x, y, and z are coordinates in a zero tilt geometry, x', y', and z' are the corresponding coordinates in the tilted gantry geometry, and $\chi$ is a shear angle of the tilted gantry geometry.

8. The method as set forth in claim 2, wherein the reconstructing step includes:

performing an n-PI reconstruction of the transformed and rebinned imaging data, where n is a positive odd integer greater than or equal to one.

9. The method as set forth in claim 8, wherein n is selected from a group of integers consisting of one and three.

10. The method as set forth in claim 8, wherein the n-PI reconstruction is selected from a group consisting of:

an exact n-PI reconstruction, and an approximate n-PI filtered backprojection reconstruction.

11. The method as set forth in claim 2, wherein a helical pitch of the volumetric helical computed tomography imaging is selected such that a point within the imaged subject is imaged on a physical detector over a contiguous 180° rotation of a radiation source.

12. The method as set forth in claim 11, wherein the physical detector is a focus-centered detector.

13. The method as set forth in claim 2, wherein the rebinning step includes:

receiving coordinates of a physical detector used in the imaging;

transforming the coordinates of the physical detector to the zero-tilt geometry wherein the transformed coordinates of the physical detector correspond to sheared detector coordinates; and rebinning the transformed imaging data to non-sheared detector coordinates based on the sheared detector coordinates.

14. The method as set forth in claim 13, wherein the transforming and rebinning steps are performed using a lookup table containing transform coefficients.

15. The method as set forth in claim 14, wherein the transform coefficients include functional parameters that depend upon a radiation source angular coordinate.

16. The method as set forth in claim 2, wherein the rebinning step reduces a fan angle of the imaging data.

17. The method as set forth in claim 2, further including:

transforming the three-dimensional image representation to the tilted gantry geometry.

18. The method as set forth in claim 17, wherein the transform used in transforming the three-dimensional image representation to the tilted gantry geometry is an inverse transform of the transform used in transforming the imaging data to a zero tilt geometry.

19. An apparatus for performing volumetric helical computed tomography imaging of a subject, the apparatus comprising:

a computed tomography scanner that acquires helical computed tomography imaging data using a tilted gantry geometry wherein a rotational plane of a rotating radiation source is tilted with respect to a direction of linear motion of the subject;

a transform processor that transforms the imaging data to a zero tilt geometry;

a rebinning processor that rebins the transformed imaging data to a non-sheared detector window; and a reconstruction processor that reconstructs the transformed and rebinned imaging data to generate a three-dimensional image representation.

20. The apparatus as set forth in claim 19, wherein the transform processor linearly transforms a sheared coordinate of the tilted gantry geometry to remove the shearing.

21. The apparatus as set forth in claim 20, wherein the linear transform of the sheared coordinate includes:

$$x_{zt} = x_{sh} - p\alpha \tan(\chi)$$

where $x_{sh}$ is the sheared coordinate, p is a constant associated with the linear motion of the subject, $\alpha$ is an angular position of the radiation source, $\chi$ is a shear angle of the tilted geometry, and $x_{zt}$ is the sheared coordinate transformed to a zero tilt geometry.

22. The apparatus as set forth in claim 19, wherein the transform processor applies a three-dimensional transform:

$$\begin{pmatrix} x' \\ y' \\ z' \end{pmatrix} = \begin{pmatrix} x + p\alpha\tan\chi \\ y \\ z \end{pmatrix}$$

where x, y, and z are coordinates in a zero tilt geometry, x', y', and z' are the corresponding coordinates in the tilted gantry geometry, p is a constant associated with the linear motion of the subject, $\alpha$ is an angular position of the radiation source, and $\chi$ is a shear angle of the tilted gantry geometry.

23. The apparatus as set forth in claim 19, wherein the reconstruction processor performs an n-PI reconstruction of the transformed and rebinned imaging data, where n is a positive odd integer greater than or equal to one.

24. The apparatus as set forth in claim 19, further including:

a rebinning lookup table in communication with the rebinning processor, the rebinning processor obtaining transform parameters from the rebinning lookup table.

25. The apparatus as set forth in claim 24, wherein the transform parameters include rebinning coefficients that depend upon a rotational angle of the radiation source.

26. The apparatus as set forth in claim 19, further including:

an image transform processor that transforms the three-dimensional image representation back to the tilted gantry geometry.

* * * * *